United States Patent
Falk et al.

(10) Patent No.: US 8,975,357 B2
(45) Date of Patent: Mar. 10, 2015

(54) SILICONE MODIFIED FATTY ACIDS, METHOD OF PREPARATION AND USAGE THEREOF

(71) Applicant: Natura Inovacao e Tecnologia de Produtos Ltda., Cajamar (BR)

(72) Inventors: Benjamin Falk, Yorktown Heights, NY (US); Jeferson A. Naue, Itatiba (BR)

(73) Assignee: Natura Inovacao e Tecnologia de Produtos Ltda., Cajamar (BR)

( * ) Notice: Subject to any disclaimer, the term of this patent is extended or adjusted under 35 U.S.C. 154(b) by 0 days.

(21) Appl. No.: 13/955,333

(22) Filed: Jul. 31, 2013

(65) Prior Publication Data

US 2013/0317105 A1    Nov. 28, 2013

Related U.S. Application Data

(63) Continuation of application No. 12/604,684, filed on Oct. 23, 2009.

(60) Provisional application No. 61/239,215, filed on Sep. 2, 2009.

(51) Int. Cl.
| | | |
|---|---|---|
| C08G 77/12 | (2006.01) | |
| A61K 8/58 | (2006.01) | |
| A61K 47/24 | (2006.01) | |
| A61Q 1/02 | (2006.01) | |
| A61Q 19/00 | (2006.01) | |
| C08G 77/38 | (2006.01) | |
| A61K 8/36 | (2006.01) | |
| C08G 77/04 | (2006.01) | |

(52) U.S. Cl.
CPC ............. *A61K 8/585* (2013.01); *A61K 47/24* (2013.01); *A61Q 1/02* (2013.01); *A61Q 19/00* (2013.01); *C08G 77/38* (2013.01); *A61K 8/361* (2013.01); *C08G 77/045* (2013.01); *C08G 77/12* (2013.01)
USPC .......................................................... 528/26

(58) Field of Classification Search
USPC .......................................................... 528/26
See application file for complete search history.

(56) References Cited

U.S. PATENT DOCUMENTS

| | | |
|---|---|---|
| 3,408,421 A | 10/1968 | Kurka |
| 3,563,941 A | 2/1971 | Plueddemann |
| 4,083,856 A | 4/1978 | Mendicino |
| 4,111,961 A | 9/1978 | Cohen et al. |
| 4,501,619 A | 2/1985 | Gee |
| 4,683,271 A | 7/1987 | Lin et al. |
| 4,725,658 A | 2/1988 | Thayer et al. |
| 4,912,242 A | 3/1990 | Revis |
| 5,051,489 A | 9/1991 | O'Lenick, Jr. |
| 5,115,049 A | 5/1992 | Imperante et al. |
| 5,136,063 A | 8/1992 | O'Lenick, Jr. |
| 5,226,923 A | 7/1993 | O'Lenick, Jr. |
| 5,258,480 A | 11/1993 | Eckberg et al. |
| 5,514,712 A | 5/1996 | Leclere |
| 5,733,533 A | 3/1998 | O'Lenick, Jr. et al. |
| 5,965,649 A | 10/1999 | Kondo et al. |
| 6,365,696 B1 | 4/2002 | Westmeyer et al. |
| 6,455,641 B1 | 9/2002 | Jost et al. |
| 6,552,212 B2 | 4/2003 | Walele et al. |
| 6,630,180 B1 | 10/2003 | Klein et al. |
| 6,646,144 B1 | 11/2003 | Klein et al. |
| 6,891,051 B1 | 5/2005 | Wohlman et al. |
| 7,084,215 B2 | 8/2006 | Dietz et al. |
| 7,153,353 B2 | 12/2006 | Ichinohe |
| 2002/0159964 A1 | 10/2002 | Nakanishi |
| 2003/0096919 A1 | 5/2003 | Ichinohe |
| 2006/0128882 A1 | 6/2006 | Ichinohe |
| 2006/0239948 A1 | 10/2006 | LaVay et al. |

FOREIGN PATENT DOCUMENTS

| | | |
|---|---|---|
| DE | 3132145 A1 | 3/1983 |
| EP | 0955340 | 11/1999 |
| GB | 369062 | 3/1932 |
| JP | 63150288 | 6/1988 |
| WO | 2006/045916 A2 | 5/2006 |
| WO | 2009/000055 A1 | 12/2008 |

OTHER PUBLICATIONS

Office Action issued May 8, 2014 in corresponding Canadian Patent Application No. 2,821,596.

*Primary Examiner* — Kuo-Liang Peng
(74) *Attorney, Agent, or Firm* — B. Aaron Schulman; Stites & Harbison, PLLC

(57) ABSTRACT

The present invention relates to silicone modified fatty carboxylic acid compounds. More specifically, the present invention is derived from low molecular weight, i.e., short chain, silicone modified fatty carboxylic acids, their use and method of making same. The present invention provides for a silicone compound partially derived from a natural product, sapucainha oil, for use in cosmetic formulations.

12 Claims, No Drawings

SILICONE MODIFIED FATTY ACIDS, METHOD OF PREPARATION AND USAGE THEREOF

CROSS-REFERENCE TO RELATED APPLICATIONS

This application is a continuation of U.S. application Ser. No. 12/604,684 filed Oct. 23, 2009, which claims priority to U.S. Application No. 61/239,215 filed Sep. 2, 2009, which is herein incorporated by reference.

TECHNICAL FIELD

The present invention relates to silicone modified fatty carboxylic acid compounds. More specifically, the present invention relates to low molecular weight, i.e., short chain, silicone modified fatty carboxylic acids, their use and method of making same.

BACKGROUND OF THE INVENTION

There is a growing trend for natural based products in the personal care, pharmaceutical and retail industry. Use of vegetable oils and waxes is well known in the art; however, they generally have non-pleasant sensorial properties for personal care products. As a result, formulators typically employ low concentrations of these materials in their formulations. Formulators also frequently include ingredients to enhance the sensorial performance of skin care and hair care products. Silicones are one class of materials that are well known in the art for enhancing the sensory properties of personal care products. Typically, a formulator might separately add a vegetable oil or wax and a silicone to a personal care product in order to achieve a desired sensory profile.

A number of silicone-modified fatty carboxylic acids are known in the art. Preparation of these prior art compounds included several processes, for example, a condensation reaction between siloxane containing hydroxyl groups and the carboxylic group of fatty acids. Another commonly used method includes hydrosilylation of olefinic esters in the presence of a metal catalyst. Another prior art process employed amino addition of an amino modified siloxane to the carboxylic group of a fatty carboxylic acid. Examples of these compounds and reactions are disclosed in, for example, U.S. Pat. No. 5,051,489 to O'Lenick, Jr., which discloses waxy lubricious solids prepared from silanol waxes for use in hair, skin and textile compositions. The compounds of this patent are prepared by reacting a silanol compound with a fatty carboxylic and or polycarboxylic acid, ester or anhydride. Another U.S. Pat. No. 5,136,063 to O'Lenick, Jr. presents a series of silicone fatty esters suitable for applications in the treatment of textile and fibers. These compounds are prepared by way of a condensation reaction between the hydroxyl containing siloxane polymer and fatty carboxylic acid, ester or anhydride. U.S. Pat. No. 5,115,049 discloses fatty carboxylic acid salts of organofunctional silicone amines. The synthesis of these compounds is performed via amino addition, where a silicone amine is neutralized by a fatty carboxylic acid. EP 0955340 discloses liquid silicone esters or blends prepared by means of hydrosilylation for use in personal care and textile softening compositions. U.S. Pat. No. 4,912,242 discloses a process for the preparation of silicon esters through the hydrosilylation of allyl esters using a metal complex catalyst. U.S. Pat. No. 4,725,658 to Thayer et al discloses silicone esters prepared by hydrosilylation of fatty esters instead of fatty acids.

Another disclosure of silicone-modified fatty acids includes U.S. Pat. No. 3,563,941, which presents a silicone-carnauba copolymer synthesized by epoxy addition of an epoxy containing siloxane to the free hydroxyl groups present in the carnauba wax. The process of this patent utilizes carnauba wax containing unreacted hydroxyl radicals. The hydroxyl radicals react with epoxy groups of the silicon-containing compounds to form silicone-carnauba wax copolymer.

In the present invention, however, it has been found that there are multiple benefits that can be obtained by first reacting a silicone with a fatty carboxylic acid and then incorporating this material into a personal, hair & skin (i.e., cosmetic composition), automotive, hard-surface, or textile enhancing composition.

An object of the present invention is therefore to provide a silicone-modified fatty carboxylic acid, i.e., silicone fatty esters, capable of imparting improved sensorial feeling on, for example, the skin or hair.

SUMMARY OF THE INVENTION

The invention provides for a cosmetic composition comprising a modified silicone compound comprising the reaction product of:

a) at least one cyclic ether silicone having the formula:

$$M_a M^A_b D_c D^B_d T_e T^C_f Q_g$$

wherein;
$M = R^1 R^2 R^3 SiO_{1/2}$
$M^A = R^4 R^5 R^6 SiO_{1/2}$
$D = R^7 R^8 SiO_{2/2}$
$D^B = R^9 R^{10} SiO_{2/2}$
$T = R^{11} SiO_{3/2}$
$T^C = R^{12} SiO_{3/2}$;
$Q = SiO_{4/2}$;

$R^1$, $R^2$, $R^3$, $R^5$, $R^6$, $R^7$, $R^8$, $R^{10}$, and $R^{11}$ are each independently a monovalent hydrocarbon radical having from 1 to 6 carbon atoms;

$R^4$, $R^9$, and $R^{12}$ are each independently a monovalent hydrocarbon radical containing from 3 to 25 carbon atoms and possessing at least one epoxy or oxetane group;

wherein subscripts a, b, c, d, e, f, and g are zero or positive and their sum is not greater than 25, with the proviso that at least one of subscripts b, d, and f is positive; and b) a substantially pure fatty carboxylic acid said fatty carboxylic acid prepared from sapucainha oil.

The present invention is based on a method for producing a modified silicone compound comprising:

i) reacting at least one cyclic ether silicone having the formula:

$$M_a M^A_b D_c D^B_d T_e T^C_f Q_g$$

wherein;
$M = R^1 R^2 R^3 SiO_{1/2}$
$M^A = R^4 R^5 R^6 SiO_{1/2}$
$D = R^7 R^8 SiO_{2/2}$
$D^B = R^9 R^{10} SiO_{2/2}$
$T = R^{11} SiO_{3/2}$
$T^C = R^{12} SiO_{3/2}$;
$Q = SiO_{4/2}$;

$R^1$, $R^2$, $R^3$, $R^5$, $R^6$, $R^7$, $R^8$, $R^{10}$, and $R^{11}$ are each independently a monovalent hydrocarbon radical having from 1 to 6 carbon atoms;

$R^4$, $R^9$, and $R^{12}$ are each independently a monovalent hydrocarbon radical containing from 3 to 25 carbon atoms and possessing at least one epoxy or oxetane group;

wherein subscripts a, b, c, d, e, f, and g are zero or positive and their sum is not greater than 25, with the proviso that at least one of subscripts b, d, and f is positive;

with a substantially pure fatty carboxylic acid derived from sapucainha oil, in the presence of at least one catalyst.

The novel fatty carboxylic acid-modified silicone of the present invention can, for example, improve the sensorial feeling on skin or hair, lower the viscosity and lower the color and the odor relative to the raw fatty acid. This silicone-modified fatty acid, i.e., silicone fatty ester, can be incorporated into cosmetic formulations in the form of emulsions, as blends with vegetable oils, and/or in a pure state.

DETAILED DESCRIPTION OF THE INVENTION

Other than in the working examples or where otherwise indicated, all numbers expressing amounts of materials, reaction conditions, time durations, quantified properties of materials, and so forth, stated in the specification and claims are to be understood as being modified in all instances by the term "about."

It will also be understood that any numerical range recited herein is intended to include all sub-ranges within that range and any combination of the various endpoints of such ranges or subranges.

It will be further understood that any compound, material or substance which is expressly or implicitly disclosed in the specification and/or recited in a claim as belonging to a group of structurally, compositionally and/or functionally related compounds, materials or substances includes individual representatives of the group and all combinations thereof.

It is further understood that the term "product" as used herein includes every conceivable use of any compound, material or substance which is expressly or implicitly disclosed in the specification and/or recited in a claim including but not limited to, pharmaceutical, medicinal and therapeutic formulations and/or compositions, skin creams, skin care lotions, moisturizers, facial treatment products, facial cleansing products, bath oils, perfumes, colognes, sachets, sunscreens, pre-shave lotions, after-shave lotions, liquid soaps, body washes, bar soaps, shaving soaps, shaving lathers, hair shampoos, hair conditioners, hair colorants, hair sprays, mousses, permanents, depilatories, cuticle coats, make-ups, color cosmetics, foundations, blushes, lipsticks, lip balms, eyeliners, mascaras, eye shadows, oil removers, cosmetic removers, delivery systems for oil and water soluble substances and all art recognized uses of product for which such silicone containing compositions, mixtures or compounds have been typically used.

In each generic structural chemical formula described and/or claimed herein wherein two or more substituents (inclusive of such terms as "groups," "functional groups," "radicals" and "moieties") are each defined as any one of several specified members, the structural formula shall be regarded as including all possible combinations of members defining all such substituents (sub-genuses) and as disclosing each combination (subgenus) as if it were individually set forth.

The cyclic ether silicone of the invention that can be reacted with fatty carboxylic acids are those which contain an epoxy bearing organic radical bonded to a silicon atom through a silicon-carbon bond. The epoxy groups are well known organic radicals and examples of organic radicals containing epoxy groups useful in the instant invention can be found through out the literature, see for example, U.S. Patent No. 3,563,941, the entire contents of which are incorporated by reference.

The cyclic ether modified silicone compounds of the invention have the general formula:

$$M_a M^A_b D_c D^B_d T_e T^C_f Q_g$$

wherein;

$M = R^1 R^2 R^3 SiO_{1/2}$ $M^A = R^4 R^5 R^6 SiO_{1/2}$ $D = R^7 R^8 SiO_{2/2}$ $D^B = R^9 R^{10} SiO_{2/2}$ $T = R^{11} SiO_{3/2}$ $T^C = R^{12} SiO_{3/2}$;

$Q = SiO_{4/2}$;

$R^1$, $R^2$, $R^3$, $R^5$, $R^6$, $R^7$, $R^8$, $R^{10}$, and $R^{11}$ are each independently a monovalent hydrocarbon radical having from 1 to 6 carbon atoms;

$R^4$, $R^9$, and $R^{12}$ are each independently a monovalent hydrocarbon radical containing from 3 to 25 carbon atoms and possessing at least one epoxy or oxetane group;

wherein subscripts a, b, c, d, e, f, and g are zero or positive and their sum is not greater than 25, with the proviso that at least one of subscripts b, d, and f is positive;

According to an embodiment of the invention, the epoxy modified silicone of the invention (i.e., general formula (1)), $R^1$, $R^2$, $R^3$, $R^5$, $R^6$, $R^7$, $R^8$, $R^{10}$, and $R^{11}$ are each independently a monovalent hydrocarbon radical having from 1 to 3 carbon atoms. In another embodiment of the invention, the epoxy modified silicone of the invention (i.e., general formula (1)), $R^1$, $R^2$, $R^3$, $R^5$, $R^6$, $R^7$, $R^8$, $R^{10}$, and $R^{11}$ are each independently a monovalent hydrocarbon radical having 1 carbon atom. According to an embodiment of the invention the sum of subscripts a, b, c, d, e, f, and g, of general formula (1), is not greater than 10. According to another embodiment of the invention, subscript b is zero, subscript a is 2, subscripts c, e, and g are zero or less than 3, and at least one of subscript d and f is positive. According to yet another embodiment of the invention, subscript b is zero, subscript a is 2, subscripts c, e, f, and g are zero and d is 1. According to yet another embodiment the present invention provides a personal care product comprising the modified silicone compound of the invention and at least one personal care product ingredient. And further according to yet another embodiment the present invention provides for a personal care product comprising the modified silicone compound of the invention prepared from sapucainha oil and at least one personal care product ingredient.

Another embodiment of the present invention provides a pharmaceutical composition comprising a modified silicone compound derived from at least one cyclic silicone and a carboxylic acid of sapucainha oil and at least one pharmaceutically acceptable carrier.

These cyclic ether silicone compounds can be prepared by hydrosilylation of an epoxy functional olefin with a hydride functional silicone. Examples may be found, for example, in U.S. Pat. Nos. 4,083,856, 6,365,696, and 5,258,480, the entire contents of which are incorporated by reference.

The following examples include, but are not limited to cyclic ether silicone compounds useful in the present invention:

According to a specific embodiment, particular cyclic ether silicone compounds useful in the preparation of the modified silicone compound of the present invention include the following:

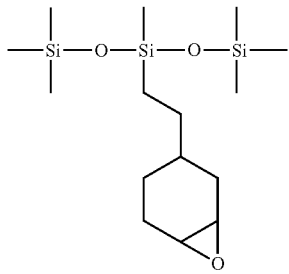

1,1,1,3,5,5,5-heptamethyl-3-[2-(7-oxa-bicyclo[4.1.0]hept-3-yl)-ethyl]-trisiloxane;

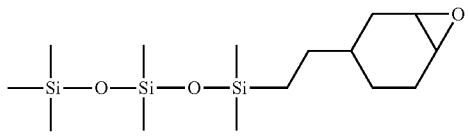 [SMILES: C[Si](C)(C)O[Si](C)(C)O[Si](C)(C)CCC1CCC2OC2C1]

1,1,3,3,5,5,5-heptamethyl-1-[2-(7-oxa-bicyclo[4.1.0]hept-3-yl)-ethyl]-trisiloxane;

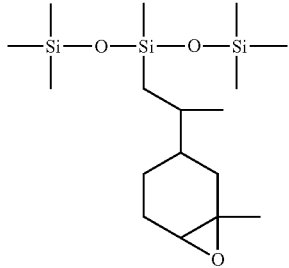

1,1,1,3,5,5,5-heptamethyl-3-[2-(1-methyl-7-oxa-bicyclo[4.1.0]hept-3-yl)-propyl]-trisiloxane;

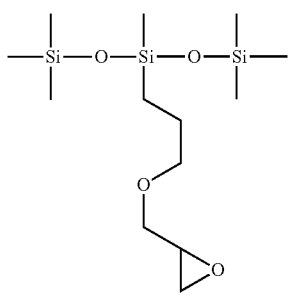

1,1,1,3,5,5,5-heptamethyl-3-oxiranylmethoxy-propyl-trisiloxane.

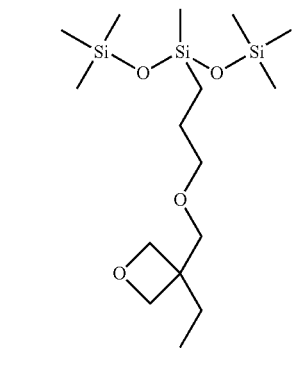

1,1,1,3,5,5,5-heptamethyl-3-(ethyl-3-propoxymethyl-oxetanyl)-trisiloxane

According to one embodiment of the invention, the number average molecular weight of the epoxy functional silicone used herein ranges from 150 g/mol to 2500 g/mol. According to another embodiment of the invention, the number average molecular weight of the epoxy functional silicone used herein ranges from 100 to 150 g/mol. According to yet another embodiment of the invention, the number average molecular weight of the epoxy functional silicone used herein ranges from 150 g/mol to 300 g/mol.

The cyclic ether silicone compounds and fatty carboxylic acids used in the invention react by the ring opening addition reaction of the carboxyl group on the fatty acid with the epoxy or oxirane group of the cyclic ether silicone compound. Since the fatty carboxylic acids contain free acid groups, i.e., —COOH, the silicone modified fatty acid copolymers contain ester linkages.

The amount of cyclic ether silicone compound used in the reaction is from about the stoichiometric equivalent, where there is not more than 1 epoxy group per 1 carboxylic acid group, or about a 1:1 to 1:10 cyclic ether silicone/fatty acid stoichiometric ratio.

The fatty acids relevant to the practice of this invention may include any fatty acid, i.e., fatty carboxylic acid, which is an aliphatic monocarboxylic acid, derived from, or contained in esterified form in an animal or vegetable fat, oil or wax. However, the fatty carboxylic acids of the invention are considered to be substantially pure fatty carboxylic acids. By "substantially pure" it is meant that the fatty carboxylic acids used herein do not contain more than 5 percent non-fatty carboxylic acid components. Exemplary non-fatty carboxylic acid components include, for example, triglycerides, ionic salts, non-functional hydrocarbons, solvents and the like, which are not fatty acids as described herein.

Natural fatty carboxylic acids commonly have a chain of 2 to 34 carbons (usually unbranched and even numbered), which may be saturated or unsaturated. However, larger fatty carboxylic acids are not common in nature or as synthetic materials.

According to an embodiment of the invention the fatty carboxylic acid used to prepare the modified silicone compound of the invention, is a hydrocarbon radical containing at least one carboxylic acid group and having from 4 to 28 carbon atoms. The hydrocarbon radical may be saturated or unsaturated. However, the use of synthetic fatty acids having at least one carboxylic acid is contemplated herein.

Another embodiment of the present invention provides a pharmaceutical composition comprising a modified silicone compound derived from at least one cyclic silicone and a carboxylic acid of sapucainha oil according to the method of the present invention and at least one pharmaceutically acceptable carrier.

Illustrative examples of fatty carboxylic acids are oleic, linoleic, linolenic, palmitic, palmitoleic, myristic, stearic, chaulmoogric, hydnocarpic, gorlic, ricinoleic, behenic, malvalic acid, sterculic acid, 2-hydroxy-sterculic acid and caprylic acid, and combinations thereof, including fatty carboxylic acids prepared by the saponification of naturally occurring esters present in animal or vegetable fats, oils or waxes, e.g. sapucainha oil. According to another embodiment of the invention, other fatty carboxylic acids are fatty carboxylic acids containing about 12 to about 24 carbon atoms and at least one carbon-carbon double bond. In still another embodiment, useful fatty carboxylic acids include, but are not limited to, the following: eleostearic acid, tall oil fatty acids, linseed oil fatty acids, tung oil fatty acids, safflower oil fatty acids, soybean oil fatty acids, and combinations thereof. Blends of fatty carboxylic acids can be used to prepare the modified silicone compounds of the invention. Examples of such blends include, but are not limited to, saponified olive oil, which typically contains the ingredients listed in Table A, below. Upon saponification of the oil the fatty carboxylic acid composition is similar in weight percent as the corresponding triglyceride in the parent compound.

TABLE A

| Free Acids | 0.3% |
|---|---|
| Oleic Acid Triglyceride | 78-83% |
| Polyunsaturated Linoleic Acid Triglyceride | 6-9% |
| Saturated Palmitic Acid Triglyceride | 8-15% |
| Stearic acid Triglyceride | 1.5-3% |

As known in the art, natural fatty carboxylic acids can be derived from or prepared by saponifying a triglyceride and removing the glycerin as a by product. Whereas, synthetic fatty acids are typically prepared by oxidizing alpha olefins.

Suitable catalysts for preparing the novel silicone modified fatty acids of the present invention include, for example, tertiary amines, quaternary ammonium hydroxides, alkali hydroxides and Lewis acids such as boron trifluoride, tin tetrachloride, aluminum trichloride and tetraisopropyl titanate. According to one embodiment of the invention, tetraisopropyl titanate is the catalyst used to prepare the silicone modified fatty carboxylic acids.

The amount of catalyst that should be used is within the range from about 0.001 to 0.1 weight percent and preferably from about 0.001 to 0.01 weight percent of the total reactant components.

The reaction can also be carried out in suitable organic solvent in order to use lower reaction temperatures. Suitable organic solvents include any neutral solvent free of active hydrogens such as esters, ethers, ketones, hydrocarbons, tertiary amines and amides. Examples of suitable organic solvents are pentane, isooctane, cyclohexane, methylcyclohexane, isohexane, n-heptane, n-octane, n-hexane, benzene, toluene, xylene, ethylbenzene, diethylbenzene, isobutylbenzene, petroleum ether, kerosene, petroleum spirits, petroleum naphtha and the like, alone or in admixture. Isopropanol is typically preferred for utilization as the organic solvent.

The compound of the present invention is best prepared by mixing a fatty carboxylic acid prepared from sapucainha oil with an epoxy containing siloxane in the presence of a suitable catalyst. If desired the solution can be heated, usually to about 80-90° C., to reduce the reaction time.

The modified silicone compound composition obtainable through the method of this invention can vary from liquid to wax in physical appearance, with light to yellow color. This silicone ester is easily incorporated in cosmetic products and the achieved benefits in the formulations are spreading, lubricity and a nice sensorial feeling on the skin and/or hair.

The modified silicone compound composition of the present invention has particular value in personal care products. Because of the unique characteristics of smoothness and sensorial feel, these compositions can be used alone, or blended with other personal care product ingredients, to form a variety of personal care products.

Examples of personal care product ingredients include, but are not limited to, ester waxes, oils and fats of animal or vegetable origin, fatty alcohols, fatty acids, alkyl esters of fatty acids; hydrocarbon oils and waxes; water, organic solvents, perfumes, surfactants, oil-soluble vitamins, water-soluble vitamins, oil-soluble drugs, water-soluble drugs, actives, pharmaceutical compounds and the like.

In particular, the modified silicone compound composition of the invention is lubricious and will improve the properties of skin creams, skin care lotions, moisturizers, facial treatments such as acne or wrinkle removers, personal and facial cleansers, bath oils, perfumes, colognes, sachets, sunscreens, pre-shave and after-shave lotions, liquid soaps, shaving soaps, shaving lathers, and the like. It can be used in hair shampoos, hair conditioners, hair oils, hair waxes, hair sprays, mousses, permanents, depilatories, and cuticle coats, and the like to enhance gloss and drying time, and provide conditioning benefits.

In addition, the modified silicone compound of the present invention exhibit a variety of advantageous and beneficial properties such as clarity, shelf stability, and ease of preparation. Hence, it has a wide application, but especially in skin care, sunscreens, antiperspirants, deodorants, in perfumes as a carrier, and for hair conditioners.

Though this invention has already been described with substantial specificity, reference is made to the following examples to characterize more specific applications of this invention.

Various embodiments of this invention are illustrated in the following examples in which all parts are by weight unless otherwise specified.

EXAMPLES AND COMPARATIVE EXAMPLES

Example 1 was prepared as follows: 65 g of 1,1,1,3,5,5,5-heptamethyl-3-[2-(7-oxa-bicyclo[4.1.0]hept-3-yl)-ethyl]-trisiloxane were charged to a 250 mL round bottom flask fitted with agitator, condenser, thermometer and nitrogen sparge. Over the epoxy modified siloxane was charged 52 grams of saponified sapucainha oil and 10 mg of titanium(IV) isopropoxide. This mixture was heated to 120° C. for 6H with nitrogen sparged lightly. At the end of the reaction, the product is cooled to ambient temperature and added to a pot. The completion of the reaction is evaluated by epoxy titration.

Comparative Example 2 was prepared as follows: 100.00 g of a polydimethylsiloxane with the average structure of $(C_6H_9O)(CH_3)_2SiO[Si(CH_3)_2O]_{20}Si(CH_3)_2(C_6H_9O)$ and 75.15 g of oleic acid was combined in a 250 g round bottom flask. The flask was blanketed with nitrogen and heated to 100° C. The flask was stirred with a magnetic stirrer. Titanium isopropoxide (0.5 mL) was added and the flask was held at 100° C. for 4 additional hours. The product was determined complete by the lack of epoxy groups determined by titration. The product was a clear yellow viscous material.

Comparative Example 3 was prepared as follows: 100.29 g of a polydimethylsiloxane with the average structure of $(CH_3)_3Si[OSi(CH_3)_2]_{40}[OSi(CH_3)(CH_2CH_2(C_6H_9O))]_{11.5}OSi(CH_3)_3$ and 127.18 g of oleic acid was combined in a 500 g round bottom flask. The flask was blanketed with nitrogen and heated to 100° C. The flask was stirred with a magnetic stirrer. Titanium isopropoxide (0.5 mL) was added and the flask was held at 100° C. for 4 additional hours. The product was determined complete by the lack of epoxy groups determined by titration. The product was a clear yellow viscous material.

Example 4 was prepared as follows: 45 g of a polydimethylsiloxane with the average structure of $(C_6H_9O)(CH_3)_2Si(CH_3)_2O[Si(CH_3)_{2.5}O_{1/2}]_2$ and 45 g of saponified olive oil was combined in a 250 g round bottom flask. The flask was blanketed with nitrogen and heated to 100° C. The flask was stirred with a magnetic stirrer. Titanium isopropoxide (0.2 mL) was added and the flask was held at 110° C. for 6 additional hours. The product was determined complete by the lack of epoxy groups determined by titration. The product was a clear orange to amber liquid.

Example 5 was prepared as follows: 43 g of a polydimethylsiloxane with the average structure of $(C_6H_9O)(CH_3)_2Si(CH_3)_2O[Si(CH_3)_{2.5}O_{1/2}]_2$ and 40 g of saponified palm oil was combined in a 250 g round bottom flask. The flask was blanketed with nitrogen and heated to 100° C. The flask was stirred with a magnetic stirrer. Titanium isopropoxide (0.2 mL) was added and the flask was held at 110° C. for 6 additional hours. The product was determined complete by the lack of epoxy groups determined by titration. The product was a clear red to amber liquid.

Formulations of Example 1 and Comparative examples 2 and 3 are presented in Tables 1 and 2 below:

TABLE 1

|  | Formulation A | Comparative Formulation B | Comparative Formulation C |
|---|---|---|---|
| Example 1 | 20% |  |  |
| Comparative Example 2 |  | 20% |  |
| Comparative Example 3 |  |  | 20% |
| Cotton Seed Oil | 80% | 80% | 80% |

TABLE 2

|  | Formulation D | Comparative Formulation E | Comparative Formulation F |
|---|---|---|---|
| Example 1 | 20% |  |  |
| Comparative Example 2 |  | 20% |  |
| Comparative Example 3 |  |  | 20% |
| Lanolin | 80% | 80% | 80% |

Application:

It is known to someone skilled in the art that the perception of tack is directly related to both viscosity and surface tension of the formulation. Listed in Table 3 below is the viscosity and surface tension of Example 1 Formulations A and D and Comparative Examples 2 and 3 Formulations B-C and E-F, respectively.

TABLE 3

|  | Surface Tension Dynes/cm | Viscosity (cPs) |
|---|---|---|
| Cottonseed Oil | 33.1 | 76.3 |
| Sunflower Oil | 33.4 | 74.5 |
| Formulation A | 24.1 | 86.2 |
| Formulation B | 23 | 99.4 |
| Formulation C | 22.9 | 106.2 |
| Formulation D | 23.9 | 80.1 |
| Formulation E | 22.9 | 94.3 |
| Formulation F | 22.5 | 99.0 |

Application:

The combination of the fatty acid modified silicone with a natural oil provides a better sensory than the natural oil alone. Displayed in the Tables 4 and 5 below are the Examples, Comparative examples and Formulations. Each Formulation was tested for tack by an eight-member panel. Each panel member placed an aliquot of each Formulation on the underside of the arm. The material was rubbed into the skin and the panel member rated each formulation on a scale of 1 to 5. 1 being the least tacky and 5 being the most.

TABLE 4

|  | Tack |
|---|---|
| Example 1 | 1 |
| Comparative Example 2 | 3 |
| Comparative Example 3 | 3.8 |

TABLE 5

|  | Tack Value |
|---|---|
| Formulation A | 1.0 |
| Formulation B | 2.0 |
| Formulation C | 1.5 |
| Cotton Seed | 1.2 |
| Formulation D | 2.2 |
| Formulation E | 2.4 |
| Formulation F | 2.4 |
| Lanolin | 3.6 |

Sensory Panel

Example 4 was blended with olive oil and tested for oiliness, tack, gloss and spreading ability by a five-member panel. Each panel member placed an aliquot of each sample on the underside of the arm. The material was rubbed into the skin and the panel member rated each sample on a scale of 1 to 5. 1 being the least tacky, oily, glossy or spreadable and 5 being the most. The control was natural olive oil.

Example 5 was tested for oiliness, gloss, tack and spreading ability by a five-member panel. The control was saponified palm oil. Each panel member placed an aliquot of Example 5 and saponified palm oil on the underside of the arm. The material was rubbed into the skin and the panel member rated each sample on a scale of 1 to 5. 1 being the least tacky, oily, glossy or spreadable and 5 being the most.

Results

Table 6 below shows the average ratings for the five-member sensory panel performed with Example 4 and its blends with olive oil. The amount of modified silicone in each formulation is expressed in weight percent. All formulations are liquid at room temperature. Table 7 below shows the average ratings for the five-member sensory panel performed with Example 5 and saponified palm oil.

TABLE 6

| Average Ratings | Control Olive oil | Blend 1 25% silicone | Blend 2 50% silicone | Blend 3 75% silicone | Example 4 |
|---|---|---|---|---|---|
| Oiliness | 4.8 | 4.0 | 3.6 | 3.8 | 3.0 |
| Tack | 1.4 | 1.4 | 1.4 | 1.6 | 1.8 |
| Gloss | 4.6 | 3.6 | 3.4 | 3.4 | 2.4 |
| Spreading ability | 4.2 | 4.2 | 4.0 | 3.8 | 4.2 |

TABLE 7

| Average Ratings | Palm fatty acid | Palm siloxane |
|---|---|---|
| Oiliness | 4.4 | 3.6 |
| Tack | 3.6 | 2.6 |
| Gloss | 2.8 | 4.0 |
| Spreading ability | 4.2 | 4.0 |

Results presented in Table 6 shows that the silicone fatty ester derived from olive oil provides less oiliness and gloss relative to the control. A decreasing range of oiliness and gloss is observed along the formulations comprising higher amounts of silicone fatty ester. Spreading ability and tack of the natural olive oil is very close to what is observed for blends comprising silicone fatty ester plus olive oil and the Example 4 tested in pure concentration. Furthermore the sensory panel revealed that Example 4 has better absorption onto the skin than natural olive oil and provides a dry touch in the skin that isn't observed with the natural oil. A lower odor is noticed too.

Results presented in Table 7 reveals that Example 5 has lower tack, oiliness and similar spreading ability relative to the palm fatty acid. On the other hand it is glossier, which usually is a desired property for hair care applications. As observed for Example 4, the silicone fatty ester derived from palm oil has better absorption onto the skin than the natural oil and presents lower odor too. Finally, results from Table 6 and 7 illustrate that the sensory feeling on the skin can be adjusted by the use of different concentrations or types of silicone-modified fatty acids.

Personal Care Formulation A containing Example 1 was prepared with the ingredients presented in Table B, below:

TABLE B

Personal Care Formulation A (Bath Oil)

| | Parts |
|---|---|
| White Mineral Oil | 80 |
| Isopropyl Myristate | 7.5 |
| Oleth-2 | 7.5 |
| Example 1 | 5 |

Personal Care Formulation A containing Example 1 was prepared as a representative bath oil formulation and was prepared in the usual and customary manner as known in the art. The addition of Example 1 to Personal Care Formulation A decreased the tack and increased the spreadability of the formulation.

Personal Care Formulation B containing Example 1 was prepared with the ingredients presented in Table C, below:

TABLE C

Personal Care Example Formulation B (Foundation Cream)

| | Parts |
|---|---|
| Phase I | |
| Stearic Acid | 12.0 |
| Isopropyl Myristate | 1.0 |
| Glyceryl Monostearate | 2.0 |
| Polysorbate 60 NF | 1.0 |
| Sorbitan Monostearate | 2.0 |
| Phase II | |
| Propylene Glycol | 12.0 |
| Pigments | 10.0 |
| Water | 56.0 |
| Phase III | |
| Silsoft 148 Silicone | 2.0 |
| Example 1 | 2.0 |

Personal Care Formulation B was prepared as a representative foundation cream and was prepared in the usual and customary manner as known in the art. Specifically, Phase I was heated to 65° C., and Phase II was then added and mixed thoroughly, followed by Phase III. The formulation was cooled to 35° C. while mixing. The addition of Example 1 to Personal Care Formulation B reduced the rub in time and tackiness of the formulation.

While the invention has been described with reference to a preferred embodiment, those skilled in the art will understand that various changes may be made and equivalents may be substituted for elements thereof without departing from the scope of the invention. It is intended that the invention not be limited to the particular embodiment disclosed as the best mode for carrying out this invention, but that the invention will include all embodiments falling within the scope of the appended claims. All citations referred herein are expressly incorporated herein by reference.

The invention claimed is:

1. A cosmetic product comprising a modified silicone compound comprising the reaction product of:

a) at least one cyclic ether silicone having the formula:

$$M_a M^A_b D_c D^B_d T_e T^C_f Q_g$$

wherein;
$M = R^1 R^2 R^3 SiO_{1/2}$
$M^A = R^4 R^5 R^6 SiO_{1/2}$
$D = R^7 R^8 SiO_{2/2}$
$D^B = R^9 R^{10} SiO_{2/2}$
$T = R^{11} SiO_{3/2}$
$T^C = R^{12} SiO_{3/2}$;
$Q = SiO_{4/2}$;

$R^1$, $R^2$, $R^3$, $R^5$, $R^6$, $R^7$, $R^8$, $R^{10}$, and $R^{11}$ are each independently a monovalent hydrocarbon radical having from 1 to 6 carbon atoms;

$R^4$, $R^9$, and $R^{12}$ are each independently a monovalent hydrocarbon radical containing from 3 to 25 carbon atoms and possessing at least one epoxy or oxetane group;

wherein subscripts a, b, c, d, e, f, and g are zero or positive and their sum is not greater than 25, with the proviso that at least one of subscripts b, d, and f is positive; and b) a substantially pure fatty carboxylic acid said fatty carboxylic acid prepared from sapucainha oil.

2. The cosmetic product of claim 1 wherein $R^1$, $R^2$, $R^3$, $R^5$, $R^6$, $R^7$, $R^8$, $R^{10}$, and $R^{11}$ are each independently a monovalent hydrocarbon radical having from 1 to 3 carbon atoms.

3. The cosmetic product of claim 1 wherein $R^1$, $R^2$, $R^3$, $R^5$, $R^6$, $R^7$, $R^8$, $R^{10}$, and $R^{11}$ are each independently a monovalent hydrocarbon radical having 1 carbon atom.

4. The cosmetic product of claim 1 wherein the sum of subscripts a, b, c, d, e, f, and g is not greater than 20.

5. The cosmetic product of claim 4 wherein subscript b is zero, subscript a is 1 to 3, subscripts c, e, and g are zero or less than 3, and at least one of subscript d and f is positive.

6. The cosmetic product of claim 4 wherein subscript b is zero, subscript a is 2, subscripts c, e, f, and g are zero and d is 1.

7. The cosmetic product of claim 1 wherein the cyclic ether silicone is at least one selected from the group consisting of 3,4-epoxycyclohexyl-1-ethane heptamethyltrisiloxane; 1,1,1,3,5,5,5-heptamethyl-3[2-(7-oxa-bicyclo[4.1.0]hept-3-yl )-ethyl]-trisiloxane; 1,1,3,3,5,5,5-heptamethyl-1[2-(7-oxa-bicyclo[4.1.0]hept-3-yl)-ethyl]trisiloxane; bisethylcyclohexyloxidepolysiloxane; 1,1,1,3,5,5,5-heptamethyl-3-[2-(1-methyl-7-oxa-bicyclo[4.1.0]hept-3-yl)-propyl]-trisiloxane; and 1,1,1,3,5,5,5-heptamethyl-3-oxiranylmethoxy-propyl-trisiloxane.

8. The cosmetic product of claim 1 wherein the amount of cyclic ether silicone compound used in the reaction is from about the stoichiometric equivalent, where there is not more than 1 epoxy or oxetane group per 1 carboxylic acid group said carboxylic acid group being the fatty carboxylic acid prepared from sapucainha oil.

9. The cosmetic product of claim 1 wherein the stoichiometric ratio of cyclic ether silicone to fatty acid used in the reaction is from about 1:1 to about 1:10.

10. The cosmetic product of claim 1 further comprising at least one personal care product ingredient.

11. The cosmetic product of claim 10 wherein the product ingredient is at least one selected from the group consisting of ester waxes, oils and fats of animal or vegetable origin, fatty alcohols, fatty acids, alkyl esters of fatty acids, hydrocarbon oils and waxes, water, organic solvents, perfumes, surfactants, oil-soluble vitamins and water-soluble vitamins.

12. A cosmetic composition comprising a modified silicone compound which is a reaction product of at least one cyclic ether silicone and a fatty carboxylic acid prepared from sapucainha oil, and at least one cosmetically acceptable carrier.

* * * * *